US008126224B2

(12) United States Patent
Zuhars et al.

(10) Patent No.: US 8,126,224 B2
(45) Date of Patent: Feb. 28, 2012

(54) METHOD AND APPARATUS FOR INSTRUMENT TRACKING ON A SCROLLING SERIES OF 2D FLUOROSCOPIC IMAGES

(75) Inventors: Joel F. Zuhars, North Andover, MA (US); Daniel E. Groszmann, Cambridge, MA (US); Tina Kapur, Andover, MA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 948 days.

(21) Appl. No.: 10/771,074

(22) Filed: Feb. 3, 2004

(65) Prior Publication Data
US 2005/0169510 A1 Aug. 4, 2005

(51) Int. Cl.
*G06K 9/00* (2006.01)
(52) U.S. Cl. ......... 382/128; 382/131; 382/154; 378/197
(58) Field of Classification Search ............... 382/131, 382/128, 154; 378/197, 62, 198, 205; 600/407, 600/424; 128/920
See application file for complete search history.

(56) References Cited

U.S. PATENT DOCUMENTS

| | | | |
|---|---|---|---|
| 5,353,354 A | | 10/1994 | Keller et al. |
| 5,431,161 A | * | 7/1995 | Ryals et al. .................. 600/425 |
| 5,823,958 A | * | 10/1998 | Truppe .......................... 600/426 |
| 5,923,727 A | * | 7/1999 | Navab .......................... 378/207 |
| 5,951,475 A | * | 9/1999 | Gueziec et al. ............... 600/425 |
| 6,102,865 A | * | 8/2000 | Hossack et al. ............... 600/459 |
| 6,263,231 B1 | * | 7/2001 | Reitter ......................... 600/425 |
| 6,360,027 B1 | * | 3/2002 | Hossack et al. ............... 382/294 |
| 6,490,475 B1 | * | 12/2002 | Seeley et al. .................. 600/426 |
| 6,511,426 B1 | * | 1/2003 | Hossack et al. ............... 600/437 |
| 6,527,443 B1 | * | 3/2003 | Vilsmeier et al. ............. 378/205 |
| 6,542,770 B2 | * | 4/2003 | Zylka et al. ................... 600/424 |
| 6,666,579 B2 | * | 12/2003 | Jensen ........................ 378/197 |
| 6,798,861 B2 | | 9/2004 | Shiota |
| 6,851,855 B2 | * | 2/2005 | Mitschke et al. ............. 378/207 |
| 6,990,220 B2 | * | 1/2006 | Ellis et al. .................... 382/128 |
| 7,050,844 B2 | * | 5/2006 | Strobel ........................ 600/424 |
| 7,176,685 B2 | * | 2/2007 | Blasche ....................... 324/309 |
| 7,471,973 B2 | * | 12/2008 | Rudy et al. ................... 600/407 |
| 2001/0027263 A1 | * | 10/2001 | Zylka et al. ..................... 600/9 |
| 2001/0051881 A1 | * | 12/2001 | Filler ............................... 705/3 |

(Continued)

FOREIGN PATENT DOCUMENTS

CN 1406117 3/2003

(Continued)

OTHER PUBLICATIONS

Japanese Preliminary Rejection, application No. 2005-025864 (4 pages) Jun. 8, 2010.

(Continued)

*Primary Examiner* — John Strege
(74) *Attorney, Agent, or Firm* — McAndrews, Held & Malloy, Ltd.; William Baxter (57) ABSTRACT

The present invention relates to a method and system apparatus for instrument tracking on a series of images. The method relates to performing instrument tracking on an image. The method comprises collecting at least one image and computing at least one of a position and orientation of at least one instrument for the at least one collected image. The method further relates to displaying at least one, some or all of the collected and computed data either separately or in any combination.

19 Claims, 3 Drawing Sheets

U.S. PATENT DOCUMENTS

| | | | |
|---|---|---|---|
| 2002/0085681 A1 | 7/2002 | Jensen | |
| 2002/0172328 A1* | 11/2002 | Dekel | 378/205 |
| 2003/0052879 A1* | 3/2003 | Barth et al. | 345/424 |
| 2004/0111024 A1* | 6/2004 | Zheng et al. | 600/426 |
| 2004/0152972 A1* | 8/2004 | Hunter | 600/424 |
| 2004/0171924 A1* | 9/2004 | Mire et al. | 600/407 |
| 2006/0269113 A1* | 11/2006 | Gundel et al. | 382/131 |

FOREIGN PATENT DOCUMENTS

| | | |
|---|---|---|
| EP | 0 595 387 A | 5/1994 |
| EP | 1347707 B1 | 5/2007 |
| JP | 2003-284059 | 10/2003 |
| JP | 3947707 B2 | 7/2007 |
| JP | 2004-517670 A | 6/2010 |
| KR | 2002-0092190 | 12/2002 |
| WO | WO 00/64367 * | 4/2000 |
| WO | 02056770 A1 | 7/2002 |

OTHER PUBLICATIONS

Communication transmitting a Partial European Search Report for Application No. 05 250 550.0-1526 dated Jun. 5, 2005, pp. 1-5.

Communication Pursuant to Article 94(3) EPC for Application No. 05 250 550.0-1526 dated Jun. 2, 2008, pp. 1-6.

Second Office Action in connection with CN Application No. 200510006476.7, from the State Intellectual Property Office, P.R. China, dated Dec. 19, 2008, pp. 1-6.

Third Office Action in connection with CN Application No. 200510006476.7, from the State Intellectual Property Office, P.R. China, dated May 22, 2009, pp. 1-6.

Text of Notice of Reexamination in connection with CN Application No. 200510006476.7, dated Nov. 8, 2010, pp. 1-4.

Korean Notice of Preliminary Rejection (English Translation ) 8 pages (Jul. 29, 2011).

* cited by examiner

METHOD AND APPARATUS FOR INSTRUMENT TRACKING ON A SCROLLING SERIES OF 2D FLUOROSCOPIC IMAGES

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

At least one embodiment of the present invention relates to instrument tracking. More specifically, at least one embodiment of the present invention relates to instrument tracking on a scrolling series of images using a display apparatus.

Computer assisted surgical procedures including instrument navigation are known. One common component of such computer assisted surgical procedures includes instrument navigation as one method for transferring knowledge of the instrument position and/or orientation to the user or operator on an ongoing basis. Traditionally, such knowledge transfer may be accomplished by acquiring static data via an imaging modality that depicts a patient's anatomy (or portion thereof). The image of an instrument may be displayed on such static data. This display may include, for example, multiple 2D fluoroscopic images, multiple 2D slices through 3D data, a 3D surface model, or other data.

It should be appreciated that such prior known computer assisted surgical procedures are limited in the manner in which the instrument position information is perceived or understood by the user. For example, in a computer assisted surgical procedure using 2D or 3D-slice planar images, the user pieces together a mental picture of the patient anatomy from the limited and distributed information provided during the procedure.

In a computer assisted surgical procedure using a 3D model, for example, the user typically looks at one particular projection of the model at a time. Looking at one projection at a time may hide significant data (including parts of the instrument) or require the removal of significant sections of the model in order to view the desired anatomy, all of which generally requires significant user interaction and visualization skills to understand the provide instrument positional information.

BRIEF SUMMARY OF THE INVENTION

At least one embodiment of the present invention relates to instrument tracking. More specifically, at least one embodiment of the present invention relates to instrument tracking on a scrolling series of images using a display apparatus.

At least one embodiment relates to a method of performing instrument tracking on an image. The method comprises collecting at least one image and computing at least one of a position and orientation of at least one instrument for the at least one collected image. The method further comprises displaying the at least one collected image, the at least one of a position and orientation of the at least one instrument and/or at least one image of the at least one instrument located at said at least one of a position and orientation.

In at least one embodiment, the method further comprises collecting at least one of a position and orientation of at least one collected image and/or at least one instrument using at least one measurement device or measurement method. The method may be used in computing the at least one position and/or orientation of the at least one instrument for the at least one collected image. It is further contemplated that each of the measurement devices may use one or more appropriate technologies, including but not limited to electromagnetic, optical, laser, and physical measurement such as via encoder feedback. It is further contemplated that each of the measurement methods may use one or more algorithmic methods, including but not limited to positional prediction methods that may or may not use phantom data, and registration methods that may or may not be entirely image-based.

Methods are contemplated which comprise collecting at least a plurality of 2D fluoroscopic images and continuously scrolling through the plurality of collected images using a display. Methods are also contemplated which comprise projecting the at least one position and orientation of the at least one instrument into the plurality of collected images in sequence.

In one or more embodiments the method comprises calibrating the at least one collected image such that the at least one position and orientation of the at least one image may be accurately displayed. In at least this embodiment, the method comprises selecting at least one calibrated image to be the current image. The method further comprises computing the at least one position and orientation for the at least one instrument for the current image.

Methods are further contemplated for using collected and/or computed measurement data of at least one of a current or past nature, from real or simulated sources, in order to compute or recompute the at least one position and/or orientation for the at least one instrument for any, some, or all of the at least one collected images, including the current image.

In still other embodiments, the method comprises collecting the at least one image using at least one image collection device that moves or is moveable. It is further contemplated that this device may be at least one C-arm which may or may not be coupled with at least one measurement device or measurement method.

Still another embodiment of the present invention relates to a method of performing instrument tracking on a series of images using a display device. This embodiment may comprise collecting a series of 2D images. The series of 2D images may be calibrated such that at least one of a position and orientation of at least one instrument may be accurately displayed in at least one image of the series of 2D images. This method may further comprise selecting at least one image of the series of 2D images to be the current image and computing the at least one position and orientation of the at least one instrument for the current image. The at least one position and orientation may be projected into the current image, which may then be displayed.

Other embodiments of the present invention comprise collecting the series of 2D images (a series of 2D fluoroscopic images for example) using an imaging device that moves or is moveable, where this device is a C-arm. For example, contemplated methods include continually scrolling through the series of images in a display, wherein at least one position and orientation of at least one instrument are projected into at least one image of the series of images. It is further contemplated that at least the current image may be incremented, wherein incrementing the current image comprises selecting a different collected image to be the current image based on an algorithm and recomputing at least one of the position and orientation of at least one instrument for the new current image.

Still another embodiment of the present invention relates to a system or apparatus for performing instrument tracking on a series of images. At least one embodiment of the apparatus comprises at least one collection device that moves or is moveable, at least one processing device and an output. In at least one embodiment, the collection device is adapted to collect the set of images. The processing device communicates with at least the collection device that moves or is moveable and is adapted to produce a scrolling series of images, at least one of the scrolling series of images including at least one of a position and orientation of at least one instrument. The output communicates with at least the processing device and is adapted to display at least one image of the scrolling series of images.

In at least one embodiment of the apparatus, the moveable collection device comprises at least one C-arm. Further, the moveable collection device comprises at least transmitter and detector devices. In at least one embodiment, the transmitter and detector devices may be used to measure the relative position and/or change in position of one or more components of the collection device with respect to objects seen within the image or images, and/or to measure the relative position and/or change in position of any instrumentation that may be present or that may be introduced into the area around the imaged objects before, during, or after the time when the moveable collection device is present in the area around the imaged objects.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references a certain embodiment of an imaging or display system, machine, apparatus or device. However, it is understood that the present invention may be used with other devices or imaging systems.

At least one embodiment of the present invention relates to instrument tracking. More specifically, at least one embodiment of the present invention relates to instrument tracking on a scrolling series of images using a display apparatus.

At least one embodiment of the present invention improves the method of transferring instrument position and/or orientation information to a user, making such information easier to use and understand. It should be appreciated that making such information easier to use and understand may improve efficiency and/or ease of use of surgical workflow and may increase product quality perception. One or more embodiments uses natural human ability to perceive 3D information from animated 2D data to transfer the position and/or orientation of a surgical instrument to the user. Previous designs have used static, non-animated data to accomplish such transfer in a method that requires substantial learned skill.

In humans, mentally perceiving a 3D volume occurs naturally when motion is introduced to a static set of data, assuming that the static set of data is suitable for animation. One or more embodiments of the present invention collects one or more (i.e., a series) of images (2D fluoroscopic images for example) using a movable collection device (a C-arm for example although other moveable collecting devices are contemplated) adapted to be rotated about a patient's anatomy of interest. It should be appreciated that, in at least one embodiment, this collected series of images or data set is appropriate for animation.

One embodiment provides feedback to the users using such data set, where the data set is continuously scrolled in a window or display, and further wherein an instrument's position and/or orientation is projected onto or into one or more images. In one embodiment, the instrument position and/or orientations are projected into or onto each image in sequence. Such scrolling of the data set, including the position and/or orientation of their instrument, enables users to understand the instrument position and/or orientation information in 3D. This takes advantage of the user's natural abilities to perceive 3D volume, thus eliminating learning new skills to understand the data. In addition, at least one embodiment does not require direct user interaction to optimize the display as required by one or more known methods of the computer assisted surgical procedures.

In at least one embodiment, the instrument may be fully displayed on one or more images of the data set without partial hiding data due to depth, as is required for 3D model instrumentation representations. This is possible as the depth perception is naturally conveyed to the user by the animation, and the position information may be fully contained within a single visualization window. This improves ease-of-use, surgical workflow and product quality perception. At least one embodiment may comprise collecting at least one of a position and orientation of at least one collected image and/or at least one instrument using at least one measurement device or measurement method. The measurement method may be used in computing the at least one position and/or orientation of the at least one instrument for the at least one collected image. It is further contemplated that each of the measurement devices may use one or more appropriate technologies, including but not limited to electromagnetic, optical, laser, and physical measurement such as via encoder feedback. It is further contemplated that each of the measurement methods may use one or more algorithmic methods, including but not limited to positional prediction methods that may or may not use phantom data, and registration methods that may or may not be entirely image-based.

In at least one embodiment measurement data of at least one of a current and past nature may be collected and/or computed, from real or simulated sources, in order to compute or recompute the at least one position and/or orientation for the at least one instrument for any, some, or all of the at least one collected images, including the current image.

Figure 1:
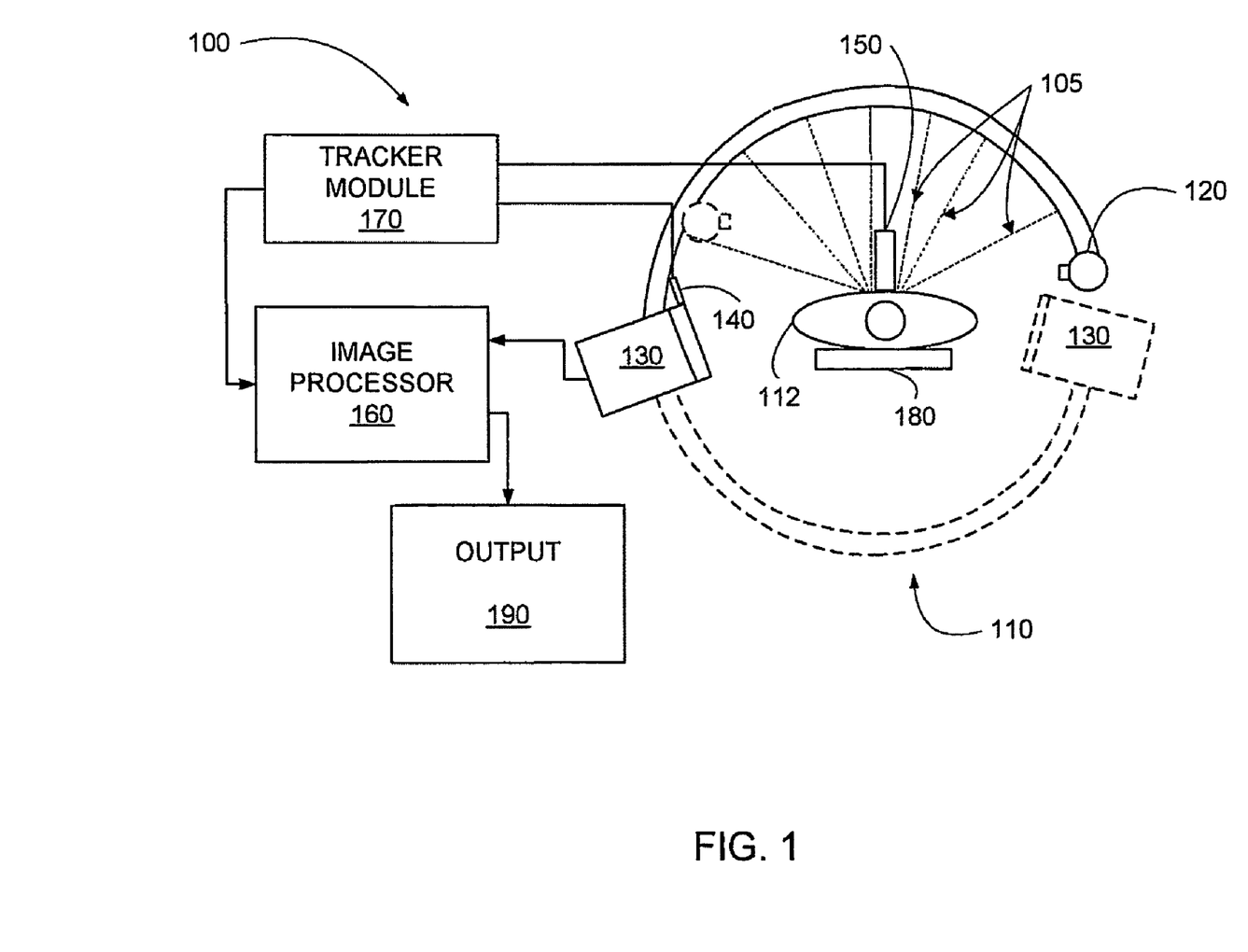
FIG. 1 illustrates an imaging or display system, device, machine or apparatus used in accordance with certain embodiments of the present invention.

FIG. 1 illustrates an imaging system, device, machine or apparatus, generally designated 100, used in accordance with at least one embodiment of the present invention. It is contemplated that system 100 may comprise a variety of systems or combinations thereof, including an X-ray system, a CT system, an EBT system, an ultrasound system, an MR system, an electromagnetic (EM) tracking system, optical tracking system, laser tracking system, encoder feedback system, algorithmic position prediction system (that may or may not use phantom data), algorithmic registration system (that may or may not be entirely image-based), or other imaging or positional measurement system.

In at least one embodiment, system 100 includes a C-arm 110, one or more X-ray sources 120, one or more X-ray detectors 130, one or more electromagnetic (EM) sensors 140, at least one EM transmitter 150, an image processing computer or device 160, a tracker module 170, a positioning device 180, and an output 190. In the illustrated embodiment, tracker module 170 is depicted communicating with at least EM sensor 140, EM transmitter 150, and image processing computer 160. FIG. 1 further illustrates image processing computer 160 communicating with at least X-ray detector 130, tracker module 170 and output 190. While the above described interconnections are illustrated, other interconnections are contemplated.

In at least one embodiment, X-ray source 120 and X-ray detector 130 are mounted on opposing sides of C-arm 110, where X-ray source 120 and X-ray detector 130 may be movably mounted on the C-arm 110. In one embodiment, EM sensor 140 is mounted on X-ray detector 130. The EM transmitter 150 is positioned on or proximate an object 112 (i.e., a patient) to be imaged. Alternatively, EM transmitter 150 may be located on the X-ray detector 130, and EM sensor 140 may be located on object or patient 112 being imaged. The object or patient 112 is positioned on or in positioning device 180. In at least one embodiment, positioning device 180 comprises a table, a table bucky, a vertical bucky, a support or other positioning device adapted to be used with the present invention.

In at least one embodiment, C-arm 110 is adapted to be moved in several directions along multiple image acquisition paths, including, for example, an orbital direction, a longitudinal direction, a lateral direction, a transverse direction, a pivotal direction and a "wig-wag" direction (where at least one example of such movement is indicated by the dashed lines in FIG. 1). In at least one embodiment, X-ray source 120 and detector 130 are movably positioned on C-arm 110 (where such moved is indicated by the dashed lines). Thus, the C-arm 110, along with X-ray source 120 and X-ray detector 130, may be moved and positioned about the positioning device 180 on or in which object 112 has been situated.

The C-arm 110 is used to position the X-ray source 120 and detector 130 about object 112 so that one or more X-rays 105 (or other energy) may irradiate object 112 to produce one or more images. The C-arm 110 may be moved or re-positioned at a variety of scan angles around object 112, obtaining a plurality of images. As the C-arm 110 moves, the distance between the X-ray detector 130 and the object 112 may vary. Further, the distance between X-ray source 120 and object 112 may also vary.

It is contemplated that, in at least one embodiment, X-ray source 120 and detector 130 on C-arm 110 may move in a cross-arm or orbital motion, for example. In an orbital motion, the X-ray source 120 and the detector 130 do not move in a circular path. In tomographic image reconstruction using orbital motion, a distance between Xray detector 130 and object 112 (and a distance between source 120 and object 112) may vary during collection of projection images.

In at least one embodiment, a position of the X-ray detector 130 may be recorded for one or more projection images. Additionally, the distance between detector 130 and the X-ray source 120 may be determined. A magnification change may be quantified and compensated for during image reconstruction using the position of detector 130 and the detector-to-object distance. The EM sensor 140 or other tracking device may be placed on detector 130. The EM transmitter 150 or other tracking device may be placed on the object 112. Data from the sensor 140 and transmitter 150 may be used to determine a position of detector 130 during a trajectory of detector 130. Other tracking devices, such as optical or mechanical tracking devices, may be used to determine a position of one or more components in the system 100.

In at least one embodiment, transmitter 150 broadcasts a signal, such as a magnetic field, that is detected by sensor 140. The tracker module 170 may use data from the transmitter 150 to determine a position of the detector 130 with respect to object 112. Differences in position and, thus, distance between the detector 130 and the object 112 correspond to differences in magnification in obtained X-ray projection images.

Changing the distance between detector 130 and object 112 and/or the distance between the source 120 and object 112 changes the magnification of the object projected onto the detector for point sources or near-point sources that emit non-parallel beams, such as X-rays. If the field of view of the X-ray source 120 is constant, as an object 112 approaches the X-ray source 120, the object 112 occupies more of the field of view and therefore projects a larger image onto the detector 130. In an embodiment, the detector-to-object distance may be varied to maintain the object 112 at a virtual isocenter of the system 100. In an embodiment, the C-arm 110 and/or the source 120 and/or detector 130 on the C-arm 110 may be moved in any plane or not moved to position the object 112 at the virtual isocenter in the field of view of the detector 130. Measurement of the varying detector-to-object and/or source-to-object distance enables the image processor 160 to compensate for the change in distance and thus the change in magnification. The tracker module 170 may use data from the EM sensor 140 and EM transmitter 150 or other tracking device to track the detector-to-object distance.

Alternatively, EM sensor 140 or EM transmitter 150 may be mounted on the source 120 with the EM transmitter 150 or EM sensor 140 on the object to determine position of the source 120. A position of the X-ray source 120 may be recorded and used with the source-to-detector distance to determine and account for the magnification change. Tracker module 170 may monitor a position and/or orientation of an instrument or tool used during a diagnostic or surgical procedure, for example.

The tracker module 170 monitors a position of at least object 112, X-ray detector 130, and/or X-ray source 120 for example. The tracker module 170 may provide position data in a reference coordinate system with respect to at least object 112, source 120, and/or detector 130. The image processor 160 may use the position data when processing the image data to reconstruct 2D and/or 3D images. The position data may also be used for other purposes, such as surgical navigation, for example. In one embodiment, the tracker module 170 calculates the positions of the X-ray detector 130 and object 112 with respect to a coordinate system defined relative to a coordinate system reference point or central axis (on a continuous basis for example). In at least one embodiment, the image processor 160 generates control or trigger commands to the X-ray source 120 or source controller to scan the object based on position data.

In at least one embodiment, the image processor 160 collects a series of image exposures from the detector 130 as the C-arm 110 is moved. The detector 130 receives an image exposure each time the X-ray source 120 is triggered. The image processor 160 combines image exposures with reference data, reconstructing a 3D volumetric data set for example. The 3D volumetric data set may be used to generate images, such as slices, or a region of interest from the object 112. For example, the image processor 160 may produce sagittal, coronal, and/or axial views of a patient spine, knee, or other area from the volumetric data sets. The image processor 160 may be implemented in software and/or hardware, where the image processor 160 may comprise a general purpose computer, a microprocessor, a microcontroller, and/or an application-specific integrated circuit, for example.

In one or more embodiments, 3D image reconstruction may be formed by combining successive slices or scanned planes of object 112 using a fan beam for example. A 3D image reconstruction may also be formed by rotating source 120 and detector 130 around object 112 to obtain cone or area beam projections of the object. In a cone beam projection, the object may be illuminated with a point source and X-ray flux measured on a plane by the detector 130. The distance from object 112 to the detector 130 and the distance from object 112 to the source 120 may be used to determine parallel projections for image reconstruction.

Filtered backprojection may also be used to reconstruct a 3D image based on filtering and backprojecting a plane in a cone beam. In a filtered backprojection, individual fan beam or cone beam projections are analyzed and combined to form a 3D reconstruction image. Fan beams are tilted out of a source-detector plane of rotation for analysis in a new coordinate system for filtered backprojection. Projection data is weighted based on distance and convolved. Then, the convolved weighted projections are backprojected over a 3D reconstruction grid to reconstruct a 3D image.

After the one or more images have been reconstructed, the image processor 160 may transmit the one or more image(s) to output 190. It is contemplated that output 190 may comprise a display, a printer, facsimile, electronic mail, a storage unit, or other medium, for example. It is further contemplated that, in at least one embodiment, output 190 may comprise a laptop, PDA, cell phone or other device wirelessly communicating with image processor computer 160. The image may be displayed and/or stored via output 190 for use by a user such as a technician, physician, surgeon, other healthcare practitioner, or security officer.

In operation, for example, a patient's mid-spinal area may be scanned in the system 100. The C-arm 110 may not reach all positions of a mid-spinal scan when the patient is positioned on a table (i.e., positioner 180). Therefore, the C-arm 110 may be moved and positioned from a side. As the C-arm 110 is moved in a non-circular motion, the spine may not remain centered in scanned images because the path of the C-arm 110 may not be circular. The C-arm 110 may be moved, such as by raising and lowering the C-arm 110 on a C-arm support, to keep the spine in the center (e.g., a virtual isocenter). As the C-arm 110 is moved and the spine is not moved, the spine is located closer to or farther from X-ray source 120. Thus, obtained images may have a different magnification from start to finish (for example, five vertebral levels in a first image to three vertebral levels in a last image due to more magnification) because the C-arm 110 moves in a non-circular arc.

A change in magnification may be determined because the position of the detector 130 with respect to the object being scanned is measured by the tracker module 170 using the EM transmitter 150 and sensor 140, for example. The magnification change may be taken into account during reconstruction of a 3D volume image of the mid-spinal area. Rather than using a fixed distance in standard image reconstruction algorithms, the variable distance values are used in reconstruction calculations for the image(s).

In at least one embodiment, the transmitter and detector devices may be used to measure the relative position and/or change in position of one or more components of the collection device with respect to objects seen within the image or images, and/or to measure the relative position and/or change in position of any instrumentation that may be present or that may be introduced into the area around the imaged objects before, during, or after the time when the moveable collection device is present in the area around the imaged objects.

As provided previously, at least one embodiment of the present invention improves the methods of transferring instrument position and/or orientation information to a user, making such information easier to use and understand. It should be appreciated that making such information easier to use and understand may improve efficiency and/or ease of use of surgical workflow and may increase product quality perception. At least one or more embodiments uses natural human ability to perceive 3D information from animated 2D data to transfer the position and/or orientation of a surgical instrument to a user.

Perceiving a 3D volume occurs naturally for humans when motion is introduced to a static set of data. One or more embodiments of the present invention collects one or more (i.e., a series) of images (2D fluoroscopic images for example) using a movable collection device (a C-arm for example) adapted to be rotated about a patient's anatomy of interest. It should be appreciated that, in at least one embodiment, this collected series of images or data set is appropriate for animation.

One embodiment provides user feedback, where the data set is continuously scrolled in a window or display. Further an instrument's position and/or orientation may be projected onto or into one or more images. In one embodiment, the instrument position and/or orientations projected into each image in sequence. Such scrolling of the data set, including the position and/or orientation of their instrument, enables the user to understand the instrument position and/or orientation information in 3D, thus taking advantage of the user's natural abilities to perceive 3D volume, thus eliminating learning new skills to understand the data. In addition, at least one embodiment does not require direct user interaction to optimize the display as required by one or more known methods of the computer assisted surgical procedures.

In at least one embodiment, the instrument may be fully displayed on one or more images of the data set without partial hiding data due to depth, as is required for 3D model instrumentation representations, since the depth perception is naturally conveyed to the user by the animation, and the position information may be fully contained within a single visualization window. This improves ease-of-use, surgical workflow and product quality perception.

Figure 2:
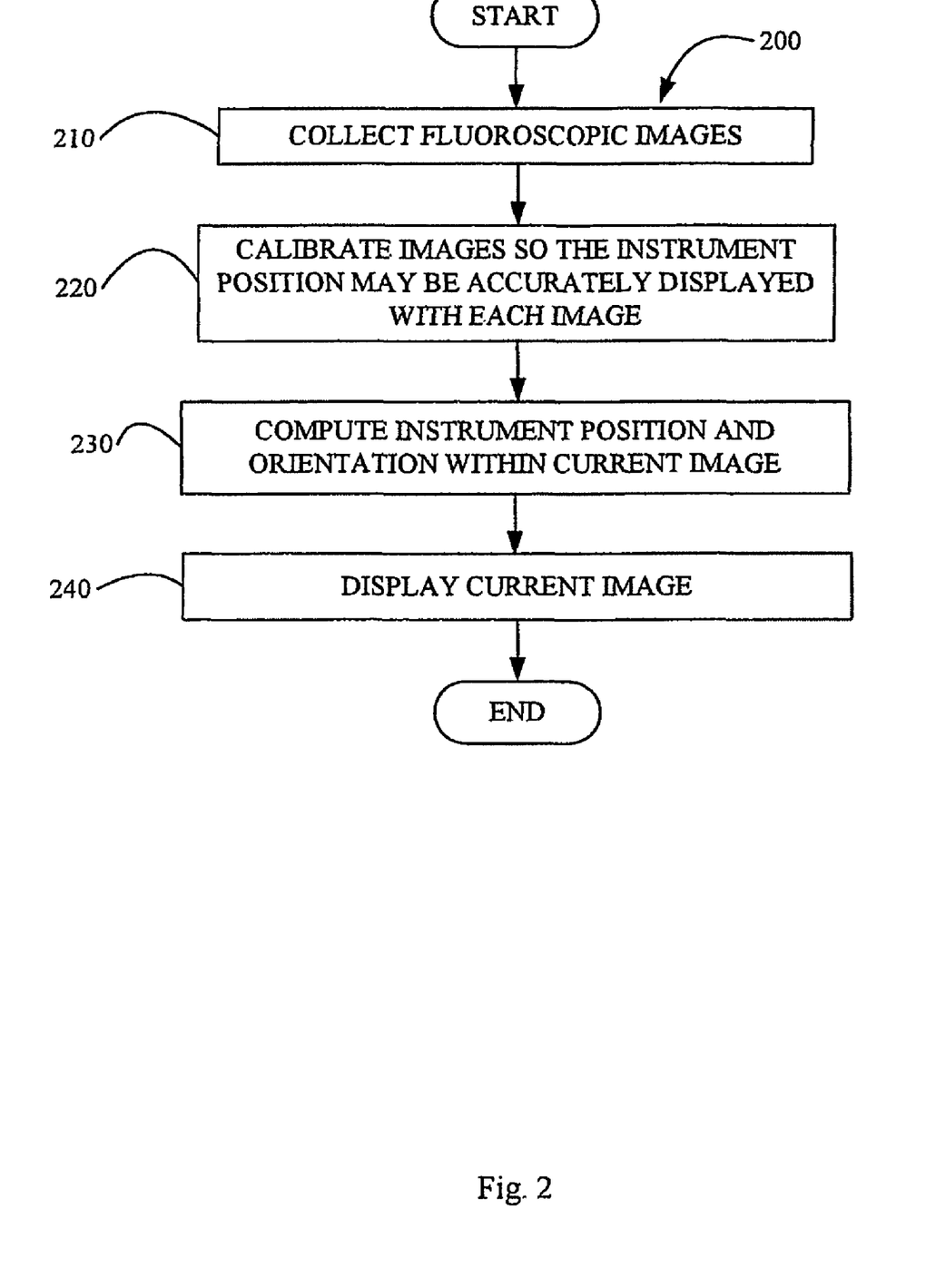
FIG. 2 illustrates a high-level flow diagram of a method of performing instrument tracking using an imaging or display apparatus similar to that depicted in FIG. 1 in accordance with certain embodiments of the present invention.

FIG. 2 illustrates a high-level flow diagram depicting a method, generally designated 200, for performing instrument tracking in accordance with certain embodiments of the present invention. In at least one embodiment, method 200 may perform such instrument tracking using an imaging system. In at least one embodiment, method 200 performs instrument tracking on a scrolling series of images using a system or apparatus similar to that depicted in FIG. 1, although other imaging systems are contemplated.

FIG. 2 illustrates method 200 comprising Step 210, collecting at least one image. In at least one embodiment, the collected image may be one or more 2D fluoroscopic images, although other images are contemplated. In at least one embodiment, method 200 may comprise rotating a collection device about or proximate a patient's anatomy of interest and collecting one or more images using a C-arm and/or detector and/or transmitter devices. Method 200 further comprises Step 220, calibrating at least one image so that a position and/or orientation of at least one instrument may be accurately displayed with such image. In at least one embodiment, Step 200 may involve image processing techniques to map image warping that is inherent to many C-arms and/or registration techniques that may or may not use objects that appear in the at least one image to determine the image position within the space of a positional measurement device.

Embodiments of the present invention further comprise Step 230, computing instrument position and/or orientation within a current image, where an instrument's position and/or orientation may be projected onto or into one or more images. Method 200 further comprises Step 240, displaying at least one collected (i.e., current) image and the position/orientation of the at least one instrument.

In one embodiment, the instrument position and/or orientations is projected into each image in sequence. Such scrolling of the data set, including the position and/or orientation of the instrument, enables the user to understand the instrument position and/or orientation information in 3D, thus taking advantage of the user's natural abilities to perceive 3D information, thus eliminating learning new skills to understand the data. In addition, at least one embodiment does not require direct user interaction to optimize the display as required by one or more known methods of the computer assisted surgical procedures.

In at least one embodiment, the instrument may be fully displayed on one or more images of the data set without partial hiding data due to depth, as is required for 3D model instrumentation representations, since the depth perception is naturally conveyed to the user by the animation, and the position information may be fully contained within a single visualization window. This improves ease-of-use, surgical workflow and product quality perception.

Figure 3:
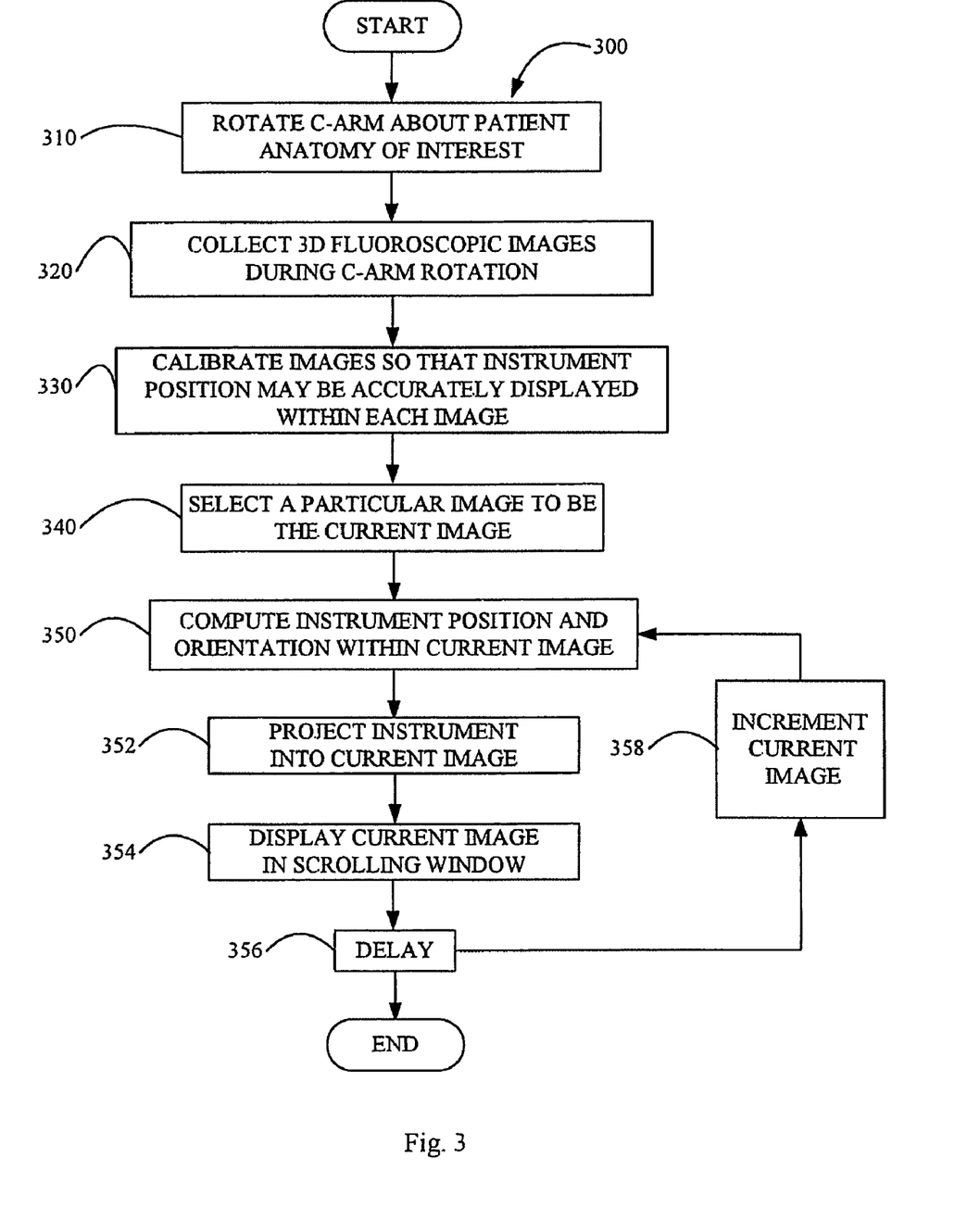
FIG. 3 illustrates a detailed flow diagram depicting a method of performing instrument tracking on a scrolling series of fluoroscopic images using an imaging or display apparatus similar to that depicted in FIG. 1 in accordance with certain embodiments of the present invention.

FIG. 3 illustrates a detailed flow diagram depicting a method, generally designated 300, for performing instrument tracking on a scrolling series of images (2D fluoroscopic images for example). In at least one embodiment, such method of performing instrument tracking uses an imaging system similar to that illustrated in FIG. 1, although other imaging systems are contemplated. In at least one embodiment, method 300 comprises Step 310, rotating a collection device (a C-arm for example) about a patient's anatomy of interest. Method 300 further comprises Step 320, collecting one or more 2D fluoroscopic images during such C-arm and/or or detector and/or transmitter devices.

Method 300, in at least one embodiment, comprises Step 330, calibrating the collected images such that one or more instrument's position and/or orientation may be accurately displayed within at least one or more images. In one or more embodiments, the instrument position and/or orientation may be accurately displayed within each such collected image. FIG. 3 further illustrates method 300 comprising Step 340 and 350. Step 340 comprises selecting a particular image to be a current image. Step 350 comprises computing position and/or orientation for at least one instrument within the current image.

Method 300 further comprises Step 352, projecting the instrument position and/or orientation into the current image. In one or more embodiments, it is contemplated that such instrument position and/or orientation may be projected into more than one image in a series of images. Step 350 comprises displaying the current image in at least one embodiment. In at least one embodiment, method 300 further comprises Step 356 and Step 358 which comprise delaying and incrementing a current image, respectively. In at least one embodiment, incrementing a current image comprises using an algorithm to select a different collected image to become the current image. This algorithm may use various parameters such as the current direction of travel through the image sequence, the desired scrolling speed and scrolling resolution, and whether the current image is at one of the ends of the image sequence to determine the next current image. After the current image is incremented, the instrument position and/or orientation may be recomputed within the new current image as illustrated in step 350.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method of performing instrument tracking on an image comprising:
    collecting in a collection device that rotatably moves a plurality of static 2D images using an image processing computer;
    computing on a tracking data processor at least one of a position and orientation of at least one instrument for said plurality of static images; and
    automatically displaying on an output device each image in said collected plurality of static 2D images in a continuous sequential image by image manner creating 3D information perceived by a user of said position and orientation of said instrument, wherein said user perceived 3D information is created by said continuous sequential image by image motion through the animation process, wherein said at least one position and orientation of said at least one instrument is projected on each said image.

2. The method of claim 1 wherein said plurality of static images comprise a plurality of 2D fluoroscopic images.

3. The method of claim 1 comprising continuously presenting the image by image animation using a display.

4. The method of claim 1 comprising calibrating at least one image of said collected plurality of static images such that said at least one position and orientation of said at least one image may be accurately displayed.

5. The method of claim 4 comprising selecting at least one calibrated image to be a current image.

6. The method of claim 5 comprising computing said at least one position and orientation for said at least one instrument for said current image.

7. The method of claim 1 comprising collecting in said collection device using a image processing computer said plurality of static images using at least one moveable collection device.

8. The method of claim 7 wherein said moveable collection device comprises a C-arm coupled to an imaging device.

9. A method of performing instrument tracking on a series of static images using an imaging device, comprising:
- collecting a series of 2D static images in a collection device that rotatably moves using an image processing computer;
- calibrating said series of 2D static images in said collection device using said image processing computer such that at least one of a position and orientation of at least one instrument may be accurately displayed in each image of said series of static images;
- selecting at least one image of said series of 2D static images to be a current image;
- computing in a tracking data processor said at least one position and orientation of said at least one instrument for said current image;
- projecting said at least one position and orientation within said current image;
- displaying said current image on an output device; and
- automatically repeating said selecting, computing, projecting, and displaying steps to create 3D information perceived by a user of said position and orientation of said instrument by creating motion through the animation process using a sequential image by image presentation of said series of 2D static images.

10. The method of claim 9 comprising collecting said series of 2D static images using a collection device that moves.

11. The method of claim 10, wherein said collection device comprises a C-arm coupled to the imaging device.

12. The method of claim 9 wherein said series of 2D static images comprise a series of 2D fluoroscopic images.

13. The method of claim 9 comprising continually using said sequential image by image presentation through said series of 2D static images in a display.

14. The method of claim 13 comprising projecting said at least one position and orientation of said at least one instrument into at least one image of said series of 2D static images.

15. The method of claim 9 comprising incrementing at least said current image.

16. The method of claim 15 comprising recomputing said at least one position and orientation of said at least one instrument.

17. An apparatus for performing instrument tracking on a series of static images, the apparatus comprising:
- a collection device that rotatably moves and is adapted to collect a series of static images using an image processing computer;
- a processing device communicating with at least said collection device and adapted to create 3D information perceived by a user by creating motion through the animation process by automatically and continuously presenting an image by image animation of said series of static images including at least one of a position and orientation of at least one instrument and at least one image of said at least one instrument located at said at least one of a position and orientation; and
- an output communicating with at least said processing device and adapted to display said image by image animation of said series of static images.

18. The apparatus of claim 17 wherein said collection device that moves comprises at least one C-arm.

19. The apparatus of claim 17 wherein said collection device that moves comprises at least one transmitter device and at least one detector device.

* * * * *